(12) United States Patent
Vanterpool

(10) Patent No.: US 7,867,523 B2
(45) Date of Patent: Jan. 11, 2011

(54) PHARMACEUTICAL COMPOSITION

(76) Inventor: Elaine A. Vanterpool, 433 Jasmine Dr., Madison, AL (US) 35757

( * ) Notice: Subject to any disclaimer, the term of this patent is extended or adjusted under 35 U.S.C. 154(b) by 369 days.

(21) Appl. No.: 12/219,245

(22) Filed: Jul. 18, 2008

(65) Prior Publication Data

US 2010/0015248 A1    Jan. 21, 2010

(51) Int. Cl.
- *A61K 31/167* (2006.01)
- *A61K 31/135* (2006.01)
- *A61K 31/315* (2006.01)
- *A61K 31/485* (2006.01)
- *A61K 31/375* (2006.01)
- *A61K 31/715* (2006.01)
- *A61K 33/30* (2006.01)
- *A61K 36/00* (2006.01)
- *A61K 36/18* (2006.01)
- *A61K 36/35* (2006.01)
- *A61K 8/97* (2006.01)

(52) U.S. Cl. .............. 424/641; 424/643; 424/769; 424/774; 424/777; 514/54; 514/289; 514/474; 514/494; 514/629; 514/648; 514/733; 514/849; 514/850; 514/888

(58) Field of Classification Search .......... 514/54, 514/289, 474, 494, 629, 648, 733, 849, 850, 514/888; 424/641, 643, 769, 774, 777
See application file for complete search history.

(56) References Cited

U.S. PATENT DOCUMENTS

| | | | |
|---|---|---|---|
| 6,586,023 B1 * | 7/2003 | Song et al. | 426/5 |
| 6,627,234 B1 | 9/2003 | Johnson et al. | 426/5 |
| 6,716,462 B2 * | 4/2004 | Prosise et al. | 426/72 |
| 6,759,062 B2 | 7/2004 | Gelber et al. | 424/726 |
| 6,841,544 B2 | 1/2005 | Gelber et al. | 514/54 |
| 6,949,264 B1 * | 9/2005 | McGrew et al. | 426/3 |
| 2002/0128273 A1 * | 9/2002 | Gelber et al. | 514/254.05 |
| 2005/0118258 A1 * | 6/2005 | Shroppolo et al. | 424/464 |
| 2007/0110676 A1 * | 5/2007 | Clymer et al. | 424/45 |

OTHER PUBLICATIONS

Catherine J. Field et al, Nutrients And Their Role in Host Resistance To Infection, Journal of Leukocyte Biology, pp. 16-32, vol. 71, Jan. 2002.
Linda S. Kim et al., Immunological Activity of Larch Arabino-Galactan and Echinacea: A Preliminary, Randomized, Double-Blind, Placebo-Controlled Trial, Alternative Medicine Review, vol. 7, No. 2, 2002, pp. 138-149.
Madeline Simasaek et al, Treatment of The Common Cold, American Family Physician, vol. 75, No. 4, Feb. 15, 2007, p. 515-520.
Thorne Research, Inc., Larch Arabino Galactan Alternative Medicine Review, vol. 5, No. 5, 2000, pp. 463-466.
Mario Roxas et al., Colds And Influenza: A Review of Diagnosis And Convential, Botanical, And Nutritional Considerations, Alternative Medicine Review, pp. 25-48, vol. 12, No. 1, Mar. 2007.
Gregory S. Kelly, Larch Arabino Galactan: Clinical Relevance of A Novel Lamine—Enhancing Polysaccharide, Alternative Medicine Review, pp. 96-103, vol. 4, No. 2, 1999.

* cited by examiner

*Primary Examiner*—John Pak
(74) *Attorney, Agent, or Firm*—Stephen R. Greiner

(57) ABSTRACT

A pharmaceutical composition for the treatment of colds and influenza. The pharmaceutical composition is a mixture of: acetaminophen, diphenhydramine, dextromethorphan, arabinogalactan, vitamin C, zinc, olive leaf extract, resveratrol and elderberry extract.

1 Claim, No Drawings

PHARMACEUTICAL COMPOSITION

FIELD OF THE INVENTION

The present invention relates generally to drug, bio-affecting and body treating compositions including plant extracts or plant materials.

BACKGROUND OF THE INVENTION

Influenza, commonly known as flu, is an infectious disease caused by a virus. In a human, symptoms of infection include: fever, sore throat, muscle pain, headache, and fatigue. In serious cases, influenza can cause pneumonia which can be fatal to weak individuals. Influenza is more severe than the common cold with symptoms sometimes lasting more than a week and is caused by a different virus. Although influenza can produce nausea and vomiting, these symptoms are more characteristic of gastroenteritis, an unrelated illness sometimes called "stomach flu."

Influenza is spread through the air by coughing or sneezing. Influenza can also be transmitted through contact with body fluids on contaminated surfaces. Influenza viruses can survive for several days at room temperature and indefinitely at low temperatures.

Minimizing contact with infected individuals prevents the spread of influenza. People who contract influenza are most infective between the second and fourteenth days after infection. Children are more infectious than adults, shedding the influenza virus at a higher rate.

Vaccinations are given to weak individuals like children and the elderly to minimize the risk of influenza infection. The most common vaccine contains inactivated material from three viruses. Unfortunately, vaccines formulated for one year can be ineffective the next since influenza viruses rapidly mutate. Thus, it is possible to get vaccinated and still get influenza.

Vaccines can cause general infection symptoms to appear, though these symptoms are usually not as severe or as long-lasting as influenza. The most dangerous side-effect of vaccination is a severe allergic reaction; however, these reactions are rare.

People with influenza are advised to get plenty of rest, drink lots of liquids, avoid using alcohol and tobacco and, if necessary, take medications such as acetaminophen to relieve fever and muscle aches. Since influenza is caused by a virus, antibiotics have no effect; unless prescribed for secondary infections such as pneumonia. Antiviral medications are sometimes effective, but viruses can develop resistance to them.

Antiviral drugs are designed to halt the spread of the virus in the body and must be taken within a few days of the onset of influenza symptoms. Different strains of influenza virus have differing degrees of resistance against these antivirals and it is impossible to predict what degree of resistance a future pandemic strain might have.

Over the counter medicines are taken to relieve influenza symptoms, but they do not affect the virus. Analgesics reduce fever, aches, pains, sinus pressure, and sore throat. Cough suppressants get rid of coughs. Also, antihistamines and decongestants minimize nasal congestion, runny nose, watery eyes, and cough. Finally, sore throats are knocked out with local anesthetics.

Homeopathic and other cold and flu remedies that fail to meet the regulatory requirements as drugs that treat disease, or the standards of evidence-based medicine, are sold as nutritional supplements. They may be based on extracts of living things, but may lack documentation of their safety and effectiveness. They may be promoted by those who deny the need for such testing and may fail to provide a scientifically plausible rationale for their effectiveness.

SUMMARY OF THE INVENTION

In light of the problems associated with the known methods and medications used to treat influenza symptoms, it is a principal object of the invention to provide a pharmaceutical composition that strengthens the immune system of an individual in order to reduce the severity and duration of symptoms associated with influenza infection. The pharmaceutical composition not only increases immune competency and function, but also treats the symptoms associated with influenza. In the end, it is believed that the composition decreases the potential for influenza to bind onto, and penetrate into, the cells of an infected individual.

It is an object of the invention to provide improved features and arrangements thereof in a pharmaceutical composition for the purposes described that is inexpensive to manufacture, safe to administer, and fast acting in effect.

Briefly, the pharmaceutical composition in accordance with this invention achieves the intended objects by featuring a mixture of: approximately 27.2 percent by weight of arabinogalactan, approximately 27.2 percent by weight of vitamin C, approximately 0.5 percent by weight of zinc, approximately 10.9 percent by weight of olive leaf extract, approximately 5.4 percent by weight of resveratrol, approximately 5.4 percent by weight of elderberry extract, approximately 21.7 percent by weight of acetaminophen, approximately 1.1 percent by weight of diphenhydramine, and approximately 0.5 percent by weight of dextromethorphan.

The foregoing and other objects, features, and advantages of the present invention will become readily apparent upon further review of the following detailed description of the preferred embodiment as illustrated in the accompanying drawings.

DETAILED DESCRIPTION OF THE PHARMACEUTICAL COMPOSITION

I have developed a pharmaceutical composition for the treatment of influenza. The composition is a mixture of nine compounds that fall into three, general groups: 1) immune system enhancers, 2) antivirals, and 3) symptom suppressants. Specifically, arabinogalactan, vitamin C, and zinc are provided in the composition to stimulate the immune system of an individual so as to better ward off influenza infections. Olive leaf extract, resveratrol and elderberry extract are provided as antiviral agents to halt the spread of influenza once it infects an individual. Finally, acetaminophen, diphenhydramine, and dextromethorphan are provided to relieve influenza symptoms.

With reference to Table 1 below, the concentration of the active compounds that comprise my pharmaceutical composition can be seen. The amounts of the compounds listed are intended for individuals being twelve years old and above and would be ingested with fluids every four to six hours while influenza symptoms persist. A smaller dose of the compound would be delivered to infants and children younger than twelve years of age.

TABLE 1

| Compound | Amount (mg) | Weight Percentage |
|---|---|---|
| Arabinogalactan | 500 | 27.2 |
| Vitamin C | 500 | 27.2 |
| Zinc | 10 | 0.5 |
| Olive Leaf Extract | 200 | 10.9 |
| Resveratrol | 100 | 5.4 |
| Elderberry Extract | 100 | 5.4 |
| Acetaminophen | 400 | 21.7 |
| Diphenhydramine | 20 | 1.1 |
| Dextromethorphan | 10 | 0.5 |

Arabinogalactan is a polysaccharide powder derived principally from the wood of the larch tree. It dissolves completely in water or juice, is low in viscosity, and is, therefore, easy to administer. It is composed of galactose and arabinose molecules in a 6:1 ratio, with a small amount of glucuronic acid. Arabinogalactan is approved by the U.S. Food and Drug Administration (FDA) as a source of dietary fiber, but also has therapeutic benefits as an immune stimulating compound.

Arabinogalactan is a safe and effective when ingested orally. Both acute and long-term toxicity studies in animals reveal no evidence of toxicity. Human consumption is usually without side-effects; however, a small percentage of individuals experience bloating and flatulence due to fermentation of arabinogalactan by intestinal microflora.

Arabinogalactan in powder form is typically dosed in tablespoons at a concentration of approximately 4-5 grams per tablespoon. The typical adult dosage is one to three tablespoons per day in divided doses; the pediatric dose is one to three teaspoons per day. The powder is usually mixed with water or juice, but can be mixed into solid food. A single dose of my pharmaceutical composition contains 500 mg. of arabinogalactan which would be consumed by an adult every four to six hours.

Ascorbic acid is also known as vitamin C. It is a crystalline compound that is soluble in water. Vitamin C is widespread in plant materials from which the concentrated form is derived. White blood cells use vitamin C to combat infections, and levels of vitamin C in the bloodstream can be depleted while fighting an infection. Thus, sick humans require outside sources of vitamin C, 500 mg. of which is provided in an adult dose of my pharmaceutical composition for consumption by an adult every four to six hours.

A recent clinical study has suggested that vitamin C can alter the function of the immune system and provide increased protection from viral infections. In the study, patients took one gram of vitamin C daily for two weeks. Researchers then analyzed the immune cell types present in the blood as well as the ability of these cells to make antiviral compounds. The number of NK cells was found to have increased while the number of T cells remained the same. The T cells, however, appeared to be more activated and produced significantly more interferon-gama, an antiviral compound. The researchers concluded that the data suggested an increase in antiviral immunity after two weeks of 1 g. per day vitamin C supplementation.

Zinc is an essential mineral that is necessary for metabolizing carbohydrates, proteins, and fats. It has been shown to support the immune system. White blood cells that help fight infection depend on zinc for their development and activation. In humans, a deficiency of zinc can result in a decreased number of white blood cells thereby reducing the ability to fight infections and heal wounds. Since it is believed that zinc shortens the duration of cold symptoms 10 mg. of zinc is provided in a single dose of my pharmaceutical composition for consumption by an adult every four to six hours.

Olive Leaf Extract is derived from the leaves of the olive tree. It is a source of many phytochemicals, primarily oleuropein. With an ability to interfere with amino acid production in viruses, olive leaf extract has been found to effectively reduce fevers and reduce the severity of viral infections. By penetrating infected cells, it is also helpful in limiting the spreading of viral infections by stopping the replication of viruses. Further, olive leaf extract appears to produce an immune system response in which cells ingest harmful microorganisms and foreign matter with enhanced vigor thereby shortening the duration of the symptoms of infection of a cold or influenza. Thus, research suggests that olive leaf extract is a "true anti-viral" compound.

Researchers recommend that large doses of olive leaf be taken. In fact, doses of up to 2000 mg per day have been found to be effective with no toxicity. A single dose of my pharmaceutical composition contains 200 mg. of olive leaf extract that would be consumed by an adult every four to six hours.

Resveratrol is a compound that is produced naturally by several types of plants and is found in the skin of red grapes. Resveratrol has also been artificially derived from Japanese knotweed and is sold as a nutritional supplement. A least one study has shown resveratrol to possess antiviral effects with resveratrol blocking the influenza virus from internally transporting proteins thereby restricting the ability of the virus to replicate. The effect was substantial when resveratrol was administered six hours after infection and continued for twenty-four hours thereafter. Interestingly, resveratrol also seems to increase the potency of some antiviral drugs.

Some animal studies have used dosages of 300 mg. per day with no observed side effects. A single dose of my pharmaceutical composition contains 100 mg. of resveratrol that would be consumed by an adult every four to six hours.

At least one recent study has shown that elderberry extract appears to reduce the severity of influenza symptoms and shorten the course of illness. The data suggests that elderberry extract inactivates the influenza virus if taken no more than two days after flu-like symptoms first appear. A small study published several years ago showed that over ninety percent of flu patients given a form of elderberry extract were symptom-free within two days with those taking a placebo recovering in about six days. Follow-up studies showed similar results with no side effects or negative interactions.

It is probable that antioxidant flavonoids contained in elderberry extract stimulate the immune system. Other compounds, called anthocyanins, have an anti-inflammatory effect leading to a reduction in aches, pains, and fever. Elderberry extract is an efficient and safe treatment for influenza symptoms in children and adults. Experts in the field suggest dosages ranging from 500 mg. to 1500 mg. per day. A single dose, taken four to six times in a given day, of my pharmaceutical composition contains 100 mg. of elderberry extract.

Acetaminophen is a widely-used painkiller and fever reducer, derived from coal tar. It is not a very effective anti-inflammatory agent, but is well tolerated and lacks many of the side-effects of aspirin. Acetaminophen is commonly used for the relief of fever, headaches, and other minor aches and pains. It is a principal ingredient in many medications for treating colds and influenza. It is considered safe for human use at recommended doses; however, overdoses can lead to fatal liver damage. A single dose of my pharmaceutical composition, taken four to six times in a given day, contains 400 mg. of acetaminophen.

Diphenhydramine hydrochloride is an over-the-counter antihistamine and sedative. Diphenhydramine was one of the first known antihistamines, invented in 1943. One dose of my pharmaceutical composition contains 20 mg. of diphenhydramine. A single dose is consumed every four to six hours by an adult as long as cold or influenza symptoms persist.

Dextromethorphan is a cough suppressant drug that is found in many over-the-counter cold and cough medicines. Pure dextromethorphan occurs as a white powder, but it is generally administered via syrups, tablets, or lozenges. Dextromethorphan provides temporary relief from coughs caused by minor throat and bronchial irritation commonly accompanying a cold. When taken at doses higher than are medically recommend, dextromethorphan acts as an hallucinogenic drug. A dose of my pharmaceutical composition, which would be taken every four to six hours while cold or influenza symptoms lasted, contains 10 mg. of dextromethorphan.

Symptoms of influenza can start suddenly one to two days after infection. Usually, the first symptoms are chills, but fevers are also common. Many individuals become so ill that they are confined to bed for several days with aches and pains. Most people who get influenza will recover in a week, and those taking the pharmaceutical composition described herein can get well in about half that time.

My pharmaceutical composition is intended use for individuals that are twelve years old and older at the dosages described above. It is expected that the composition, in a powdered form at the time of manufacture, would be enclosed in water-soluble gelatin capsules for consumption by individual users. Depending on their volume, one or two capsules would contain a single dose of the composition.

For use, the number of capsules making up a single dose of the pharmaceutical composition would be swallowed with a liquid every four to six hours while the symptoms of a cold or influenza last. Alternatively, every four to six hours, the capsule(s) containing a single dose of the pharmaceutical composition would be mixed into a glass of liquid and swallowed within fifteen minutes. No more than six doses of the pharmaceutical composition should be consumed by an individual in a single day. No side effects should be experienced when taking the maximum recommended dose.

It is expected that certain individuals will consult a doctor before taking the pharmaceutical composition. In particular, individuals who are: pregnant, nursing, very young, and very old should have the approval of a doctor. Also, individuals with medical conditions such as: asthma, cardiovascular disease, diabetes, and immune deficiencies should speak with a physician prior to taking the pharmaceutical composition.

A trial of the pharmaceutical composition was conducted with one patient being an eleven month-old boy infected with influenza. Typically, during the three- to five-day incubation of a viral illness, such as a cold, the patient experiences a cough that progresses from mild to croupish. The croup lasts between one and two weeks, during which time the original viral illness runs its course and requires treatment with an oral steroid to reduce its severity. By providing the pharmaceutical composition to the patient to treat a normal viral illness, the patient returned to a healthy condition in four days with minimal coughing. The progress of the patient's illness is summarized in Table 2 provided below.

TABLE 2

| Day | Doses Per Day | Symptom(s) | Severity | Notes |
| --- | --- | --- | --- | --- |
| 1 | 1 | Sore throat, Cough, Runny Nose | Mild-Bad | Trial Starts |
| 2 | 2 | Sporadic Cough | Mild | N/A |
| 3 | 2 | Sporadic Cough | Mild | N/A |
| 4 | 1 | Infrequent Cough | Very Mild | N/A |
| 5 | 1 | No Symptoms | N/A | Patient Usually has Croup at this Time |
| 6 | 0 | No Symptoms | N/A | Viral Illness Over |

The size of each dose of the pharmaceutical composition delivered to the patient whose viral illness is outlined in Table 2 was approximately 2.8 percent of the size of the adult dosage noted hereinabove. The "infant sized" dose was dissolved in five (5) ml. of liquid. No side effects related to the ingestion of the pharmaceutical composition by the patient were observed.

From the data collected in Table 2, it is concluded that the pharmaceutical composition described herein has the potential to prevent the onset of the severity of a cold and has the ability to shorten the duration of a cold. Furthermore, the pharmaceutical composition appears to prevent the onset of complications related to colds since the patient did not develop croup or a sinus infection during the course of his viral illness.

While my pharmaceutical composition has been described with a high degree of particularity, it will be appreciated by those skilled in the art that modifications can be made to it. For example, the respective amounts of the active compounds comprising the pharmaceutical composition can be increased or decreased depending, for example, on the weight, age, gender and physical condition of the intended recipient. Further, the active compounds can be combined with other active compounds or inert binders and fillers not described herein. Therefore, it is to be understood that the present invention is not limited solely to the pharmaceutical composition described above, but encompasses any and all pharmaceutical compositions within the scope of the following claims.

I claim:

1. A pharmaceutical composition, comprising a mixture of:
approximately 27.2 percent by weight of arabinogalactan;
approximately 27.2 percent by weight of vitamin C;
approximately 0.5 percent by weight of zinc;
approximately 10.9 percent by weight of olive leaf extract;
approximately 5.4 percent by weight of resveratrol;
approximately 5.4 percent by weight of elderberry extract;
approximately 21.7 percent by weight of acetaminophen;
approximately 1.1 percent by weight of diphenhydramine; and,
approximately 0.5 percent by weight of dextromethorphan.

* * * * *